(12) United States Patent
Poll et al.

(10) Patent No.: US 8,623,665 B2
(45) Date of Patent: Jan. 7, 2014

(54) FECAL SAMPLE COLLECTION AND PROCESSING APPARATUS AND METHOD

(76) Inventors: Val L. Poll, Ogden, UT (US); Steven J. Miller, Hyrum, UT (US); Jay J. Davis, Smithfield, UT (US); Brian T. Leishman, Wellsville, UT (US); Joshua L. Kirk, Providence, UT (US)

( * ) Notice: Subject to any disclaimer, the term of this patent is extended or adjusted under 35 U.S.C. 154(b) by 34 days.

(21) Appl. No.: 13/273,112

(22) Filed: Oct. 13, 2011

(65) Prior Publication Data

US 2012/0028296 A1    Feb. 2, 2012

Related U.S. Application Data (63) Continuation-in-part of application No. 12/766,786, filed on Apr. 23, 2010, now abandoned, which is a continuation-in-part of application No. 12/577,560, filed on Oct. 12, 2009, now abandoned.

(51) Int. Cl.
*G01N 1/18* (2006.01)

(52) U.S. Cl.
USPC ........... 436/177; 422/422; 422/549; 422/560; 422/408; 436/43; 436/174; 436/179

(58) Field of Classification Search
USPC .................................. 422/408, 422, 549, 560
See application file for complete search history.

(56) References Cited

U.S. PATENT DOCUMENTS

| | | | |
|---|---|---|---|
| 4,175,008 A | 11/1979 | White | |
| 4,225,423 A * | 9/1980 | Cotey | ................................ 209/3 |
| 4,312,950 A | 1/1982 | Snyder et al. | |
| 4,387,725 A | 6/1983 | Mull | |
| 4,409,988 A | 10/1983 | Greenspan | |
| 4,735,905 A | 4/1988 | Parker | |
| 4,789,639 A | 12/1988 | Fleming | |
| 4,801,547 A | 1/1989 | Rosenberg | |
| 4,961,432 A | 10/1990 | Guirguis | |
| 5,066,463 A * | 11/1991 | Chang | ........................... 422/408 |
| 5,326,398 A | 7/1994 | Kelley et al. | |
| 5,431,884 A | 7/1995 | McDonough et al. | |
| 5,440,942 A | 8/1995 | Hubbard | |
| 5,480,484 A | 1/1996 | Kelley et al. | |
| 5,624,554 A | 4/1997 | Faulkner et al. | |
| 5,730,147 A | 3/1998 | Craig | |
| 6,063,038 A | 5/2000 | Diamond et al. | |
| 6,180,395 B1 | 1/2001 | Skiffington et al. | |

(Continued)

FOREIGN PATENT DOCUMENTS

EP    0175326 A2    3/1986

OTHER PUBLICATIONS

Fecal Examination Using "Fecalyzer" Brand Fecal Float, http://cal.vet.upenn.edu, Copyright 2004, pp. 1-2.

*Primary Examiner* — Sally Merkling
(74) *Attorney, Agent, or Firm* — Pate Peterson, PLLC; Warren M. Pate (57) ABSTRACT

A method for collecting and processing biological samples (e.g., fecal samples) is disclosed. The method may include obtaining a system comprising a container, a collector, and a lid. Using the collector, a user may collect a sample. The sample may be inserted within the container. The lid may be secured and the container and sample contained therewithin may be transported to a testing facility. At the testing facility, the container may be used throughout the processing of the sample. Accordingly, the risk of cross-contamination may be reduced.

19 Claims, 11 Drawing Sheets

(56) References Cited

U.S. PATENT DOCUMENTS

| | | |
|---|---|---|
| 6,207,113 B1 | 3/2001 | Kagaya |
| 6,299,842 B1 | 10/2001 | Kozak et al. |
| 6,524,530 B1 | 2/2003 | Igarashi et al. |
| 6,582,665 B2 | 6/2003 | Faulkner |
| 6,612,767 B2 | 9/2003 | Muller |
| 6,653,149 B1 | 11/2003 | Tung et al. |
| 6,780,160 B2 | 8/2004 | Zhou et al. |
| 6,921,370 B2 | 7/2005 | Zhou et al. |
| 7,048,693 B2 | 5/2006 | Zhou et al. |
| 7,141,033 B2 | 11/2006 | Kanjilal et al. |
| 7,163,514 B2 | 1/2007 | Zhou et al. |
| 7,300,632 B2 | 11/2007 | Sugiyama et al. |
| 7,338,634 B2 | 3/2008 | Chang |
| D567,373 S | 4/2008 | Irby |
| 2003/0175167 A1 | 9/2003 | Takanori |
| 2006/0115385 A1 | 6/2006 | Meyer |
| 2009/0258411 A1 | 10/2009 | Petithory et al. |
| 2009/0291818 A1 | 11/2009 | Soares et al. |
| 2011/0048981 A1 | 3/2011 | Okumura |
| 2011/0083495 A1 | 4/2011 | Poll et al. |
| 2011/0085948 A1 | 4/2011 | Poll et al. |

\* cited by examiner

FECAL SAMPLE COLLECTION AND PROCESSING APPARATUS AND METHOD

RELATED APPLICATIONS

This application is a continuation-in-part of U.S. patent application Ser No. 12/766,786 filed Apr. 23, 2010 (now abandoned), which is a continuation-in-part of U.S. patent application Ser. No. 12/577,560 filed Oct. 12, 2009 (now abandoned). U.S. patent application Ser. No. 12/766,786 and U.S. patent application Ser. No. 12/577,560 are both hereby incorporated by reference.

BACKGROUND

1. The Field of the Invention

The present invention relates generally to a device, assembly, and method employed in the collection and analysis of samples or specimens and, more specifically, the collection and analysis of fecal or other biological matter.

2. The Background Art

Various methods and devices have been used in the past to collect, transport, and test biological samples. Many such samples are fecal samples taken by veterinarians or technicians at veterinary clinics. The standard practice for collecting, transporting, and testing a fecal sample typically involves transferring the sample from one container to another several times. However, each time the sample is transferred, there is an increased risk of compromising (e.g., contaminating) the sample. The high volume of samples being tested in laboratories further compounds this risk.

In view of the foregoing, it would be advantageous to provide a sample collection assembly that limits, or even eliminates, the risk of compromising or contaminating a sample during collection, transport, and testing. Further, it would be advantageous to provide a sample collection assembly that is less tedious and messy and improves the efficiency of laboratory technicians.

BRIEF SUMMARY OF THE INVENTION

In view of the foregoing, in accordance with the invention as embodied and broadly described herein, a method and apparatus are disclosed in one embodiment of the present invention as including a specimen collection, transport, and testing system. In selected embodiments, a system in accordance with the present invention may limit or eliminate the need for transferring a sample or solution derived therefrom from one container to another.

In certain embodiments, a system may include a container having an open end and a closed end. The system may further include a collector, filter, lid, and the like or combinations or sub-combinations thereof. In selected embodiments, a collector may include a loop facilitating the collection of a sample of suitable size. A filter may be sized and configured to be positioned within the container. In selected embodiments, a filter may selectively engage a distal end of a collector. A lid may be selectively applied to cover the open end of a container. A lid may secure a sample, collector, filter, or some combination or sub-combination thereof within a container.

In selected embodiments, a filter may include a central portion and a filter portion. A central portion may connect to a distal end of a collector. A filter portion may surround at least a portion of the distal end of the collector. A filter portion may include multiple openings extending therethrough.

A filter may include a nub extending therefrom. Such a nub may engage an aperture located in a distal end of a collector. Alternatively, a distal end of a collector may include a nub extending therefrom. This nub may engage an aperture located in a filter. Accordingly, a filter may be selectively applied to a collector and removed thereof by a user as desired.

In operation, a user may obtain a system in accordance with the present invention. The system may include a container, collector, filter, lid, and the like or combinations or sub-combinations thereof. Using the collector, a user may collect a sample (e.g., fecal sample). A user may then (1) apply a filter to a distal end of the collector, (2) insert the filter, collector, and sample within a corresponding container, and (3) secure a lid in place to capture the filter, collector, and sample within the corresponding container. The system and sample contained therein may then be transported to a testing facility (e.g., laboratory).

Alternatively, no filter may be needed or desired. Accordingly, after using a collector to collect a sample, a user may (1) insert the collector and accompanying sample within a corresponding container and (2) secure a lid in place to capture the collector and sample within the corresponding container. The system and sample contained therein may then be transported to a testing facility.

At a testing facility, a liquid (e.g., a liquid facilitating processing of a sample) may be passed (e.g., injected) through an opening in a lid to at least partially fill a corresponding container. The sample and surrounding liquid may be agitated, which may disperse the sample within the liquid. The collector and filter (or simply the collector in embodiments that do no include a filter) may then be removed from the container.

In embodiments employing a filter, removal of the filter may support or provide removal of various solids from within a container. That is, located at a distal end of a collector, a filter may be distal to any solid debris or undissolved portions of a sample. Accordingly, as a collector and filter are removed from a container, the filter may remove the solid debris or undissolved portions from the container while permitting the liquid and dissolved portions of the sample to remain in the container.

Once a collector (or collector and filter combination) has been removed from a container, the contents remaining in the container may be subjected to additional processes or steps consistent with the testing being performed. In selected embodiments, these additional processes may include subjecting the container and its content to separation within a centrifuge, adding additional liquid to the container to bring floating parasite identifiers (e.g., parasite eggs) and the like to the opening of the container, placing a cover slip across the opening to collect floating parasite identifiers, placing the cover slip on a slide, and placing the slide under a microscope to identify and count the various parasite identifiers collected. Accordingly, the container of a system in accordance with the present invention may used throughout the collection, transport, and testing of a sample.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF SELECTED EMBODIMENTS

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

Figures 1, 2:
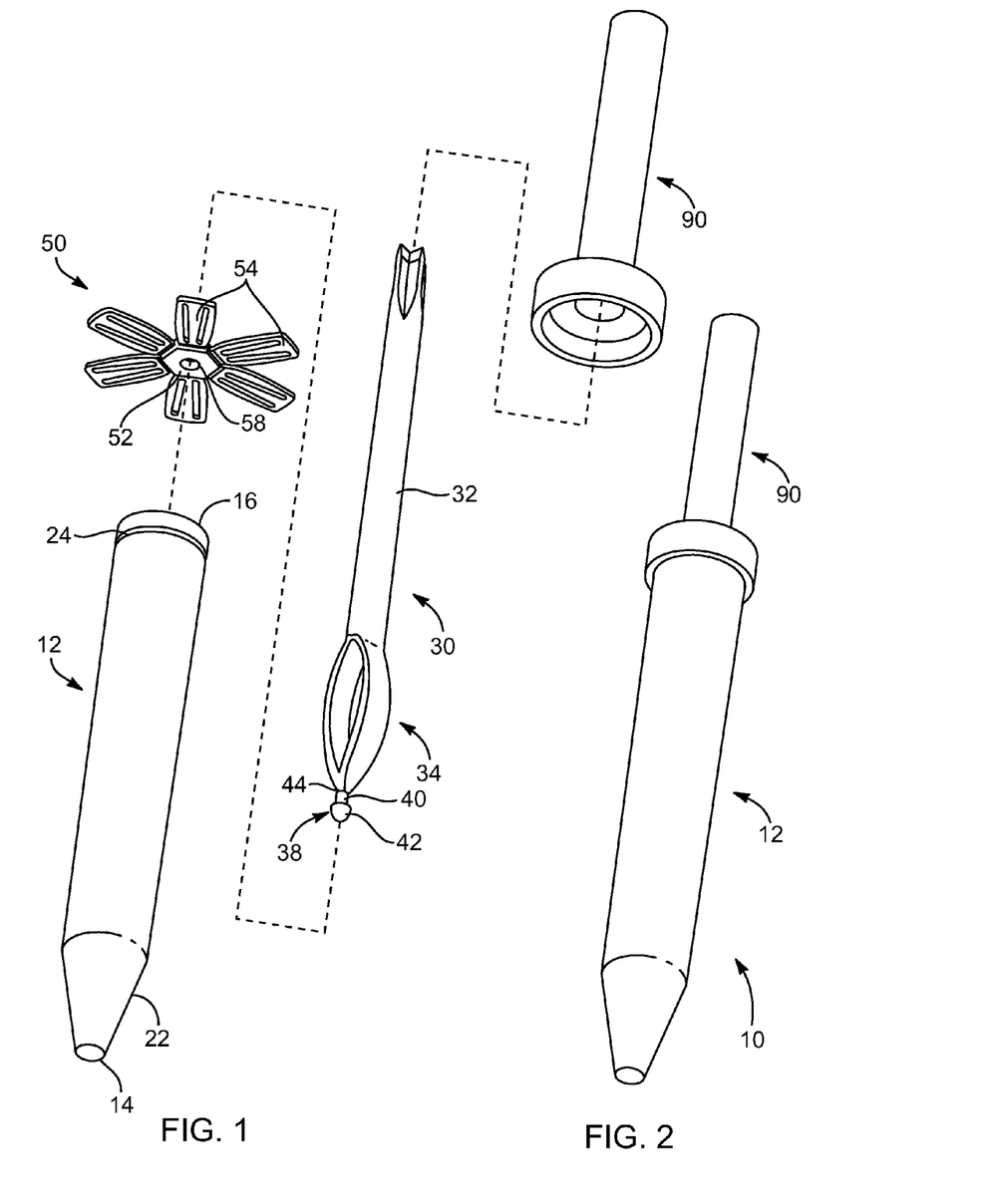
FIG. 1 is an exploded view of one embodiment of a sample collection and processing system comprising a container, collector, filter, and lid in accordance with the present invention.
FIG. 2 is a perspective view of the system of FIG. 1 in an assembled configuration.
Figure 3:
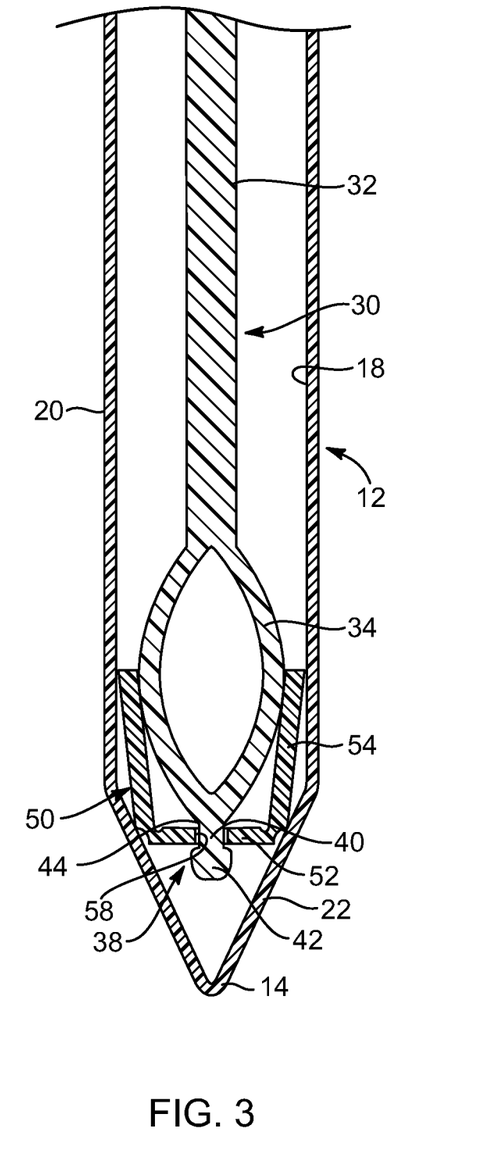
FIG. 3 is a cross-sectional view of a distal portion of the system of FIG. 1.
Figure 4:
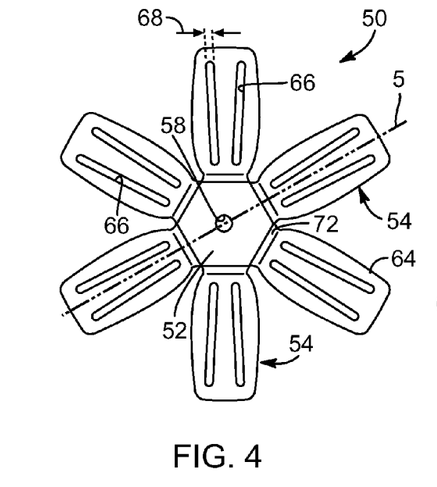
FIG. 4 is a top plan view of the filter of FIG. 1.
Figure 5:
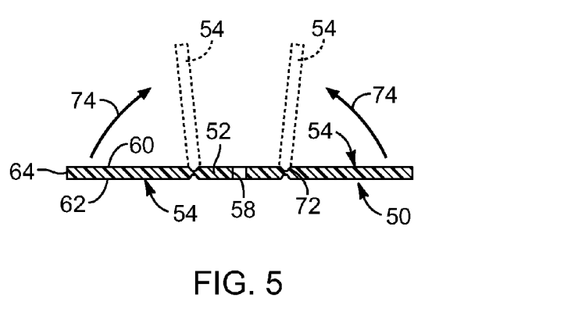
FIG. 5 is a cross-sectional view of the filter of FIG. 1.
Figure 6:
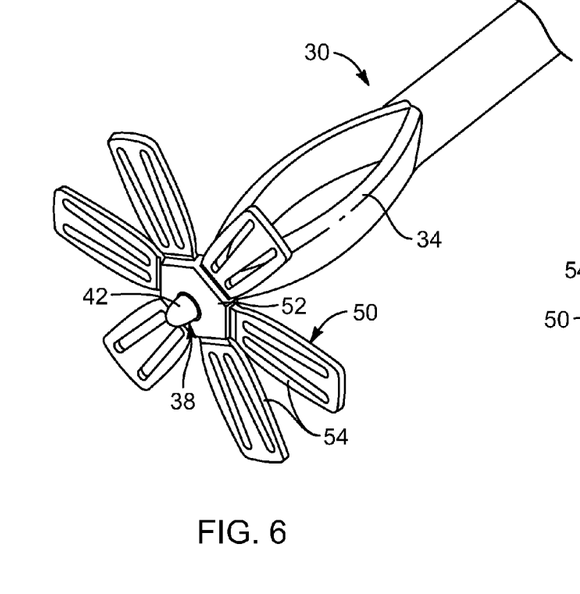
FIG. 6 is a perspective view of the filter of FIG. 1 attached in an extended configuration to a distal end of the collector of FIG. 1.
Figure 7:
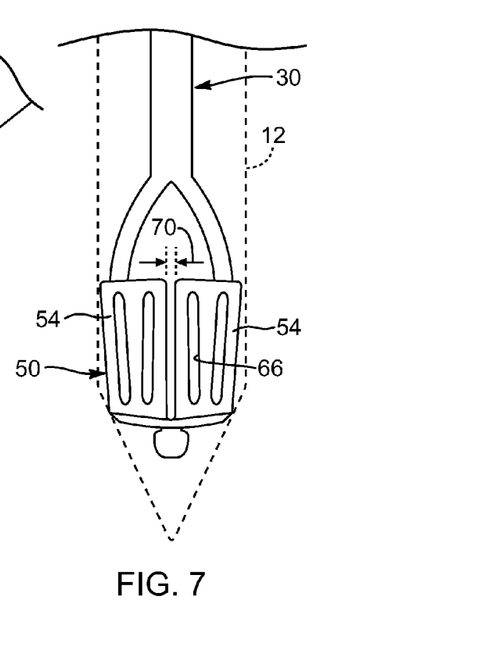
FIG. 7 is a side view of the filter of FIG. 1 attached in a deflected configuration to a distal end of the collector of FIG. 1.

Referring to FIGS. 1-3, a system 10 in accordance with the present invention may be employed to minimize the steps and cost in collecting and processing samples (e.g., fecal samples) in the field and laboratory. A system 10 may also minimize the risk of compromising and/or contaminating a sample due to transferring the sample from one container to another.

A system 10 in accordance with the present invention may include a container 12, collector 30, filter 50, and lid 90. A container 12, collector 30, filter 50, or lid 90, or combinations or sub-combinations thereof, may be formed from any suitable material or combination of materials. In selected embodiments, one or more components may be formed from polymeric materials or thermoplastics. Suitable polymers may include Polypropylene (PP), High Density Polyethylene (HDPE), Low Density Polyethylene (LDPE), or the like. Such components may be formed in any suitable manner. For example, one or more components may be formed and manufactured utilizing techniques such as injection molding, thermo-forming, plastic stamping, machining, or the like.

A container 12 in accordance with the present invention may have any suitable shape. In selected embodiments, a container 12 may have a cylindrical or tubular shape with one end 14 closed and the other end 16 open. A container 12 may include a taper 22 or conical portion 22 converging proximate a closed end 14. A container 12 may include an inner surface 18 and an outer surface 20. An outer surface 20 may include a detent mechanism 24 (e.g., a raised ring extending circumferentially around a container 12) proximate an open end 16. A detent mechanism 24 may assist in retaining a lid 90 in engagement with a corresponding container 12.

A collector 30 may include an elongate portion 32 and a collection portion 34. A collector 30 may be sized and configured to allow a person to grasp the elongate portion 32 and collect, with the collection portion 34, a sample (e.g., collect a fecal sample from a mammalian body). A collection potion 34 may have any suitable shape or configuration. The shape or configuration of the collection portion 34 may depend on the nature of the sample being collected. For example, to facilitate collection of fecal samples, a collection portion 34 may comprise or resemble a typical fecal loop. Alternatively, a collection portion 34 may comprise a different structure. For example, a collection portion 34 may comprise a swab, spoon, flat surface, fork, piercing element, or the like.

In selected embodiments, after a collector 30 has been used to obtain a sample, the collector 30 may engage or connect to a filter 50. This engagement may be accomplished in any suitable manner. For example, a collector 30 may include a fastener 38 (e.g., extension nub 38) sized and configured to selectively engage (and disengage) an aperture 58 in a corresponding filter 50. A filter 50 may include a central portion 52 and multiple filter tabs 54 extending away from the central portion 52. In selected embodiments, a central portion 52 may contain or define an aperture 58 for engaging or receiving a fastener 38 extending from a collector 30.

In certain embodiments, a fastener 38 may include a neck 40 and a head 43 extending away from a distal end 44 of a collector 30. The fastener 38 may be sized and shaped to engage an aperture 58 in a filter 50 with a snap-type connection. Alternatively, a fastener 38 may include threads for engaging corresponding threads formed in an aperture 58 in a filter 50.

Referring to FIGS. 4-7, a filter 50 may include a first side 60, a second side 62, and a periphery 64 or edge 64 extending between the first and second sides 60, 62. The shape or configuration of the first and second sides 60, 62 may be similar or substantially identical. The periphery 64 or edge 64 may define a plurality of filter tabs 54.

Filter tabs 54 may extend radially away from a central portion 52 of a filter 50. In selected embodiments, a central portion 52 may have a hexagonal configuration. In such embodiments, one filter tab 54 may extend from each of the six sides. In other embodiments, a central portion 52 may be a different shape (e.g., triangular, square, octagonal, round, or the like). Each filter tab 54 may include one or more openings 66 extending therethrough. Openings 66 may be sized and configured to facilitate a filtering function. In selected embodiments, openings 66 may have an elongated shape defining a width 68, or any other shape or configuration, to provide desired filtering characteristics.

In certain embodiments, filter tabs 54 may be positioned in an expanded configuration before a corresponding filter 50 has been inserted within a container 12. However, as such a filter 50 is inserted within a container 12, the corresponding filter tabs 54 may deflect 74. The ability of the filter tabs 54 to deflect 74 may be enhanced by a thin wall 72 forming the interface between each filter tab 54 and a corresponding central portion 52. A thin wall 72 may function as a living hinge.

In selected embodiments, a thin wall 72 may be symmetrical. That is, each filter tab 54 may deflect 74 with substantially equal ease in either direction. Accordingly, there may be no requirement for a first side 60 or a second side 62 of the filter 50 to be positioned adjacent a collector 30. Either side 60, 62 may be so positioned with substantially equal functionality and performance.

When a filter 50 is inserted within a container 12, the filter tabs 54 may deflect to achieve a deflected configuration. In a deflected configuration, adjacent filter tabs 54 may be spaced from one another a distance 70 comparable (e.g., substantially equal) to the width 68 of the openings 66. Accordingly, the spacing 70 between filter tabs 54 may provide a filtering function similar to that of the openings 66 within the filter tabs 54.

In selected embodiments, the side walls or periphery 64 of each filter tab 54 may be slightly curved so that when placed within a container 12, the spacing 70 between filtering tabs 54 may be substantially constant along a length of each filter tab 54. In certain embodiments, the width 68 of the openings 66 within a filter tab 54 and the spacing 70 between adjacent filter tabs 54 may be about 0.02 inches to about 0.04 inches and preferably about 0.025 inches to about 0.035 inches.

In certain alternative embodiments, filter tabs 54 or a filter 50 may include one or more screen members or portions of screen material providing a more precise filtering action. In still other alternative embodiments, a filter 50 may be preformed in a cup-like configuration. In such a configuration, a filter 50 may be interconnected and no deflection 74 may be necessary. The central portion 52 of a filter 50 may form the bottom of a cup, while the side wall provides a filter portion. A fastener 38 may extend to engage the bottom of the cup. The side wall may then surround at least a distal portion of a collector 30.

Figure 8:
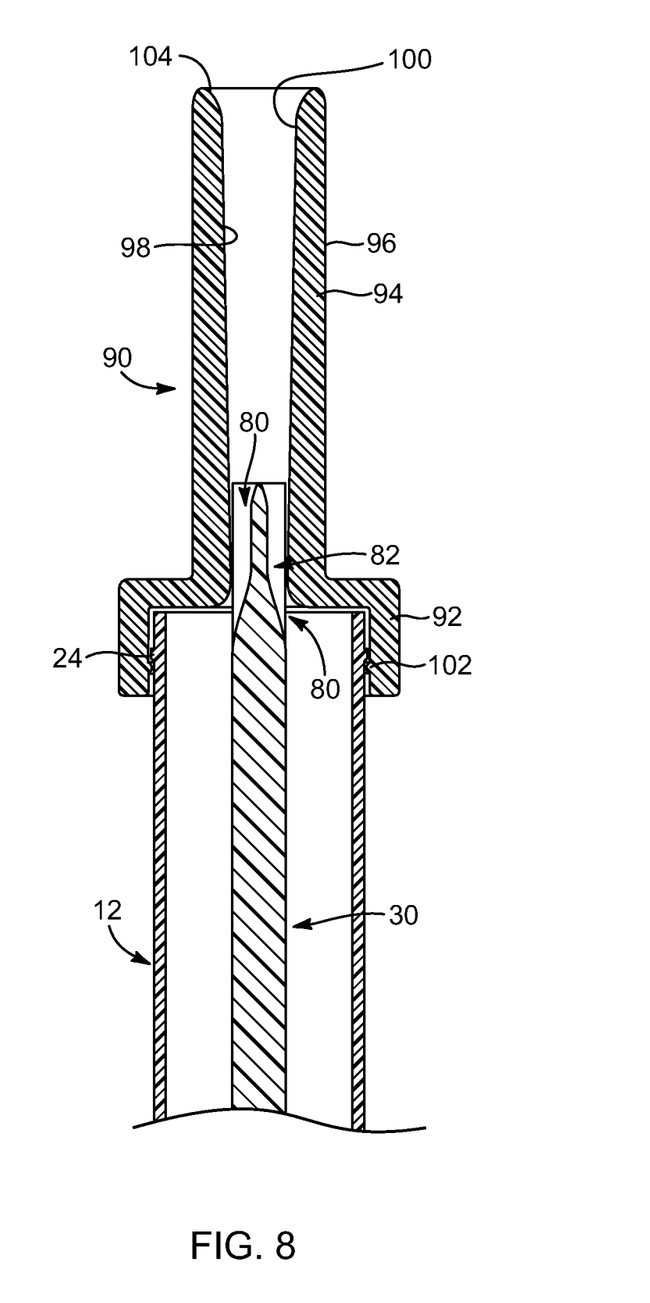
FIG. 8 is a cross-sectional view of a proximal portion of the system of FIG. 1.
Figures 9, 10:
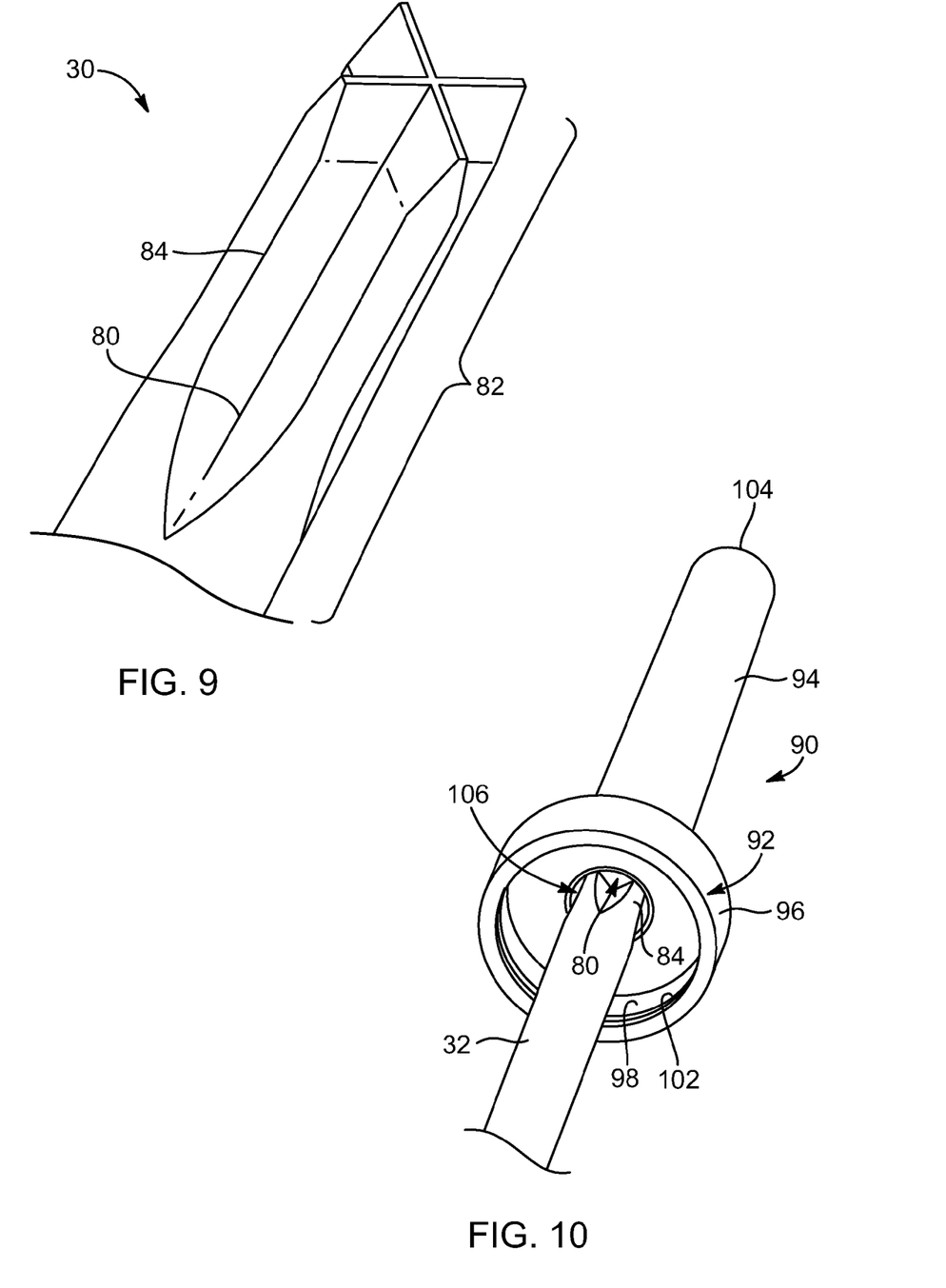
FIG. 9 is a perspective view of a proximal end or portion of the collector of FIG. 1.
FIG. 10 is a perspective view of a proximal end or portion of the collector of FIG. 1 engaging the lid of FIG. 1.

Referring to FIGS. 8-10, in selected embodiments, a lid 90 may include a cap portion 92 and a handle portion 94. A cap portion 92 may be sized and configured to close an open end 16 of a container 12. For example, an inner surface 98 of a lid portion 92 may include a detent mechanism 102 (e.g., a ridge) sized and configured to engage a corresponding detent mechanism 24 of a container 12. Such an engagement may assist in maintaining a lid 90 properly secured with respect to a container 12.

In certain embodiments, a lid portion 92 and a handle portion 94 of a lid 90 may both include an outer surface 96 and an inner surface 98. An inner surface 98 may define a conduit 100 extending through the length of a handle portion 94. A conduit 100 may extend between a proximal end or opening 104 and a distal end or opening 106 to define a path through a lid 90.

A handle portion 94 of a lid 90 may be sized and configured to at least partially capture a proximal portion 82 or end 82 of an elongate portion 32 of a collector 30. For example, a distal opening 106 and conduit 100 defined in a handle portion 94 may be sized and configured to receive, in a snug manner, at least a portion of a proximal end 82 of the elongate portion 32. In selected embodiments, an inner surface 98 of a handle portion 94 may contact and grip one or more ridges 84 formed in a proximal portion 82 of a collector 30.

With a handle portion 94 sized and configured to at least partially receive the proximal end 82 of a collector 30 therewithin, a portion of one or more channels 80 (e.g., spaces between adjacent ridges 84) may be exposed to allow fluid to pass therethrough. For example, such channels 80 may be sized and configured to pass liquid (e.g., a liquid or processing solution employed during a testing procedure) therethrough. Accordingly, without removing a lid 90 or collector 30 from a container 12, liquid may be passed through the proximal opening 104 at one end of the lid 90, through the conduit 100, along the channels 80, and into the container 12.

A channel 80 may extend and be defined in a handle portion 32 as a ravine-like structure, a tunnel, or the like. In selected embodiments, a collector 30 may include four channels 80 extending in parallel. In one embodiment, each channel 80 may be defined by a ridge 84 extending along each side thereof. A channel 80 may extend along a longitudinal length of an elongate portion 32. Alternatively, a channel 80 may extend only within a proximal portion 82 of an elongate portion 32.

Figure 11:
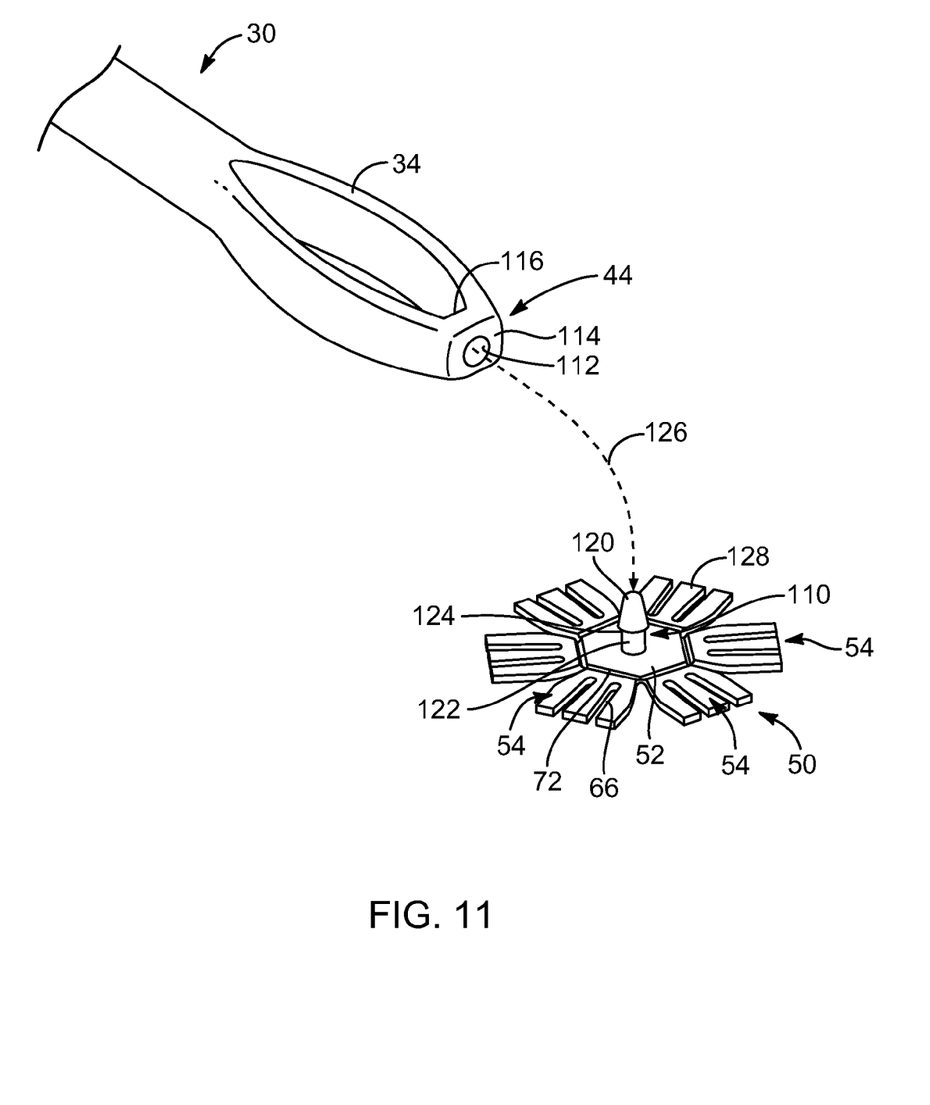
FIG. 11 is a partial perspective view of an alternative embodiment of a filter and collector in accordance with the present invention.
Figure 12:
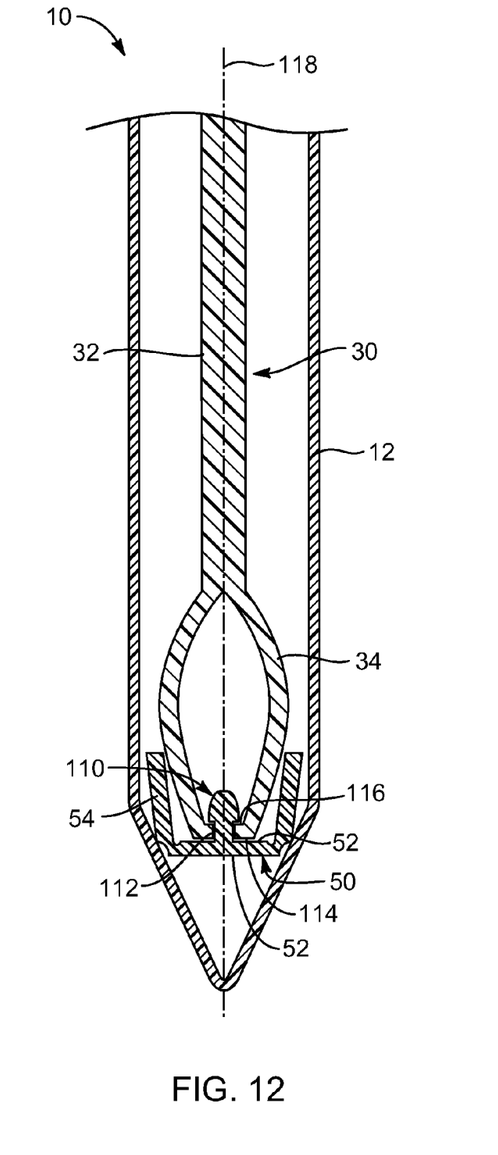
FIG. 12 is a cross-sectional view of a distal portion of the filter and collector of FIG. 11 inserted within a container in accordance with the present invention.

Referring to FIGS. 11 and 12, any suitable mechanism may be employed to attached a filter 50 to a collector 30. As described hereinabove, in selected embodiments, a collector 30 may include a fastener 38 extending to engage an aperture 58 in a filter 50. In other embodiments, a filter 50 may include a fastener 110 extending to engage an aperture 112 in a collector 30.

For example, in certain embodiments, a distal end 44 of a collector 30 may include an exterior surface 114 (e.g., a flat exterior surface 114) and an interior surface 116 (e.g., a flat interior surface 116). An aperture 112 may extend through the distal end 44 from an exterior surface 114 to an interior surface 116. An interior surface 116 may provide an edge or lip to assist in latching or engaging a fastener 110 of a filter 50. Alternatively, an aperture 112 may comprise a recess in an exterior surface 114 that does not reach or breach any interior surface 116. Such a recess may include one or more ridges defined therein to assist in latching or engaging a fastener 110 of a filter 50. An aperture 112 may extend co-axially along a longitudinal axis 118 of a collector 30.

A central portion 52 of a filter 50 may include a fastener 110 extending therefrom. In selected embodiments, a fastener 110 may comprise an extension nub 110 extending from one side of a filter 50. For example, a fastener 110 may include a neck 120 and a head 122 with a ridge 124 defined between the neck 120 and the head 122. A head 122 may include a somewhat oval or round shape with a diameter slightly larger than a diameter of the aperture 112 defined in a corresponding collector 30. A neck 120 may include a height that is about equal to or slightly greater than a depth of a corresponding aperture 112.

In operation, an aperture 112 may be positioned over 126 a fastener 110. The aperture 112 may be manually pressed over the fastener 110, thereby attaching a filter 50 to a collector 30. For example, as it slides through an aperture 112, the head 120 of a fastener 110 may slightly deform. However, once the head 120 extends completely through the aperture 112, a ridge 124 or lip 124 portion of the fastener 110 may engage or abut an interior surface 116. Accordingly, a fastener 110 may securely connect a filter 50 to a collector 30. However, should a user need to remove a filter 50 from a collector 30, the engagement between the ridge 124 and the interior surface 116 may be overcome without structural damage using a reasonable force.

In selected embodiments, tabs 54 of a filter 50 may define openings 66 therein that extend to an outer periphery 128. For example, each opening 66 may define an elongate channel that is open to the outer periphery 128 of the tabs 128. The tabs 54 in such embodiments may be shorter in length than the previously described embodiments (e.g., less than half the length of the collection portion 34 of a corresponding collector 30). Such tabs 54 may provide more volume for a solution to mix with a sample adhering to the collection portion 34 of a collector 30. Other structures, functions, and the like of such tabs 54 and corresponding filter 50 may be similar to the previously described embodiments.

Figure 13:
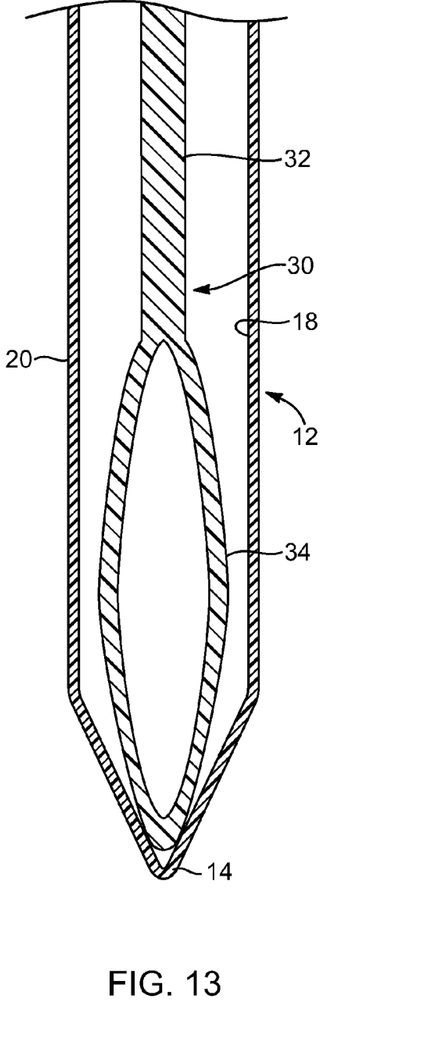
FIG. 13 is a cross-sectional view of a distal portion of one embodiment of a filter-less system in accordance with the present invention.

Referring to FIG. 13, in selected embodiments, various components or portions thereof may be omitted from a system 10 in accordance with the present invention. For example, a filter 50 may be omitted. This may be done by simply selecting a collector 30, using the collector 30 to collect a sample, inserting the sample and collector 30 within a container 12, and securing a lid 90. The collector 30 used in such filter-less embodiments may be configured to receive or engage a filter 50. For example, the collector 30 may include a fastener 38, aperture 112, or the like. Alternatively, the collector 30 may be devoid of such mechanisms 38, 112.

The size of a collection portion 34 of a collector 30 may vary between embodiments. In selected embodiments, the size of the collection portion 34 may be varied to control the size of a sample collected thereby. For example, in certain embodiments, a collection portion 34 may comprise a loop sized to collect a sample of about 0.5 grams. In other embodiments, a collection portion 34 may comprise a loop sized to collect a sample of about 1.0 grams. In still other embodiments, a collection portion 34 may comprise a loop sized to collect a sample of about 1.0 to about 2.0 grams.

Figure 14:
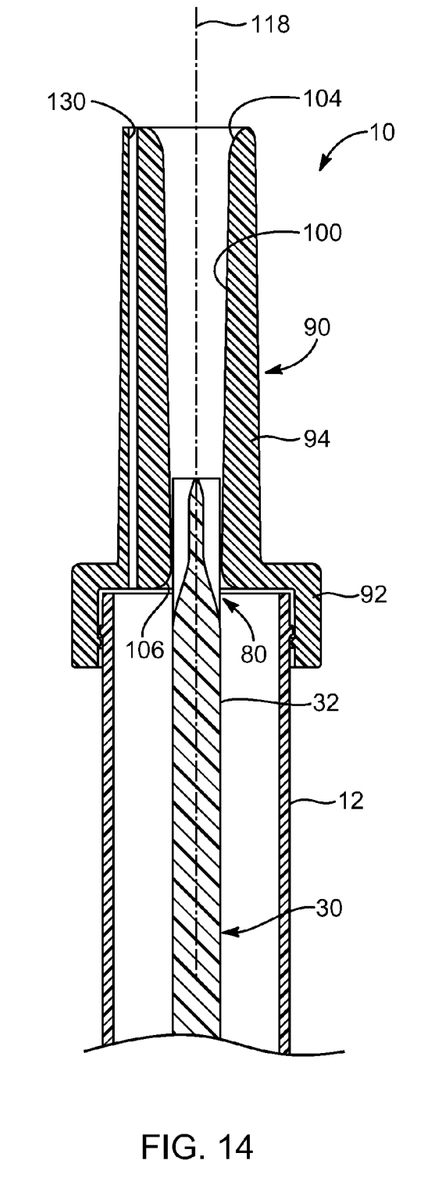
FIG. 14 is a cross-sectional view of one embodiment of a proximal portion of a system having a vented lid in accordance with the present invention.
Figure 15:
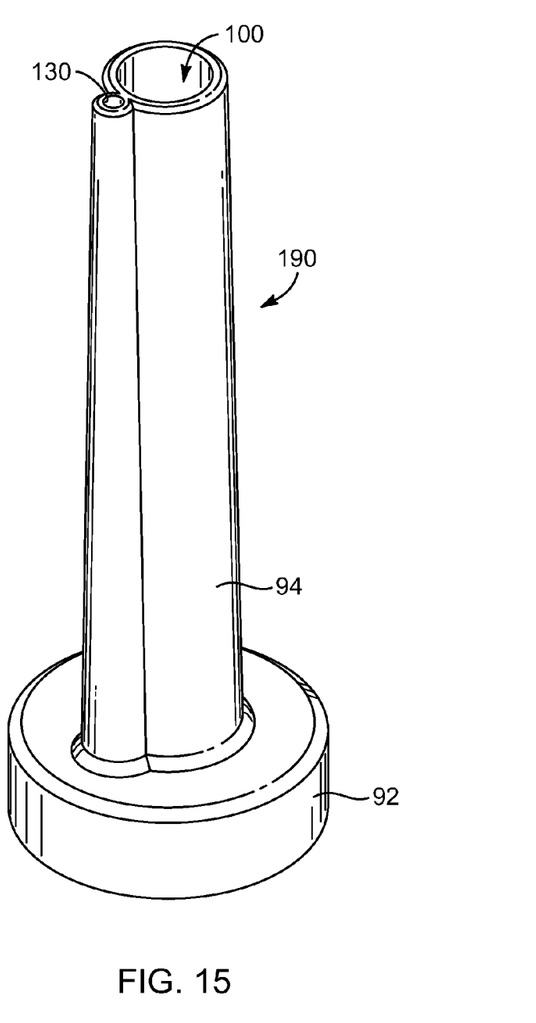
FIG. 15 is a perspective view of the lid of FIG. 14.

Referring to FIGS. 14 and 15, in selected embodiments, a lid 190 may include a vent 130. A vent 130 may extend directly through the wall of a cap portion 92. Alternatively, a vent 130 may extend along a longitudinal length of a handle portion 94 of a lid 90. For example, a vent 130 may extending in parallel with a conduit 100 located within a handle portion 94 of a lid 90. In operation, when liquid is inserted through a conduit 100, a vent 130 may provide a passageway for displaced air to escape a container 12. Accordingly, a vent 130 may be sized to the accommodate the expected flow rate of the displaced air.

In selected embodiments, a lid 90 may include one or more removable plugs or covers. When installed, a plug may cover a proximal opening 104, vent 130, or some combination thereof. A plug may be employed during transport of a system 10 and the sample contained therewithin. A plug may assist in maintaining the integrity of the sample and prevent the sample from drying out before testing. Once a system 10 and corresponding sample have arrived at a testing facility, a plug may be removed to allow the insertion of a processing liquid within the system 10.

Figure 16:
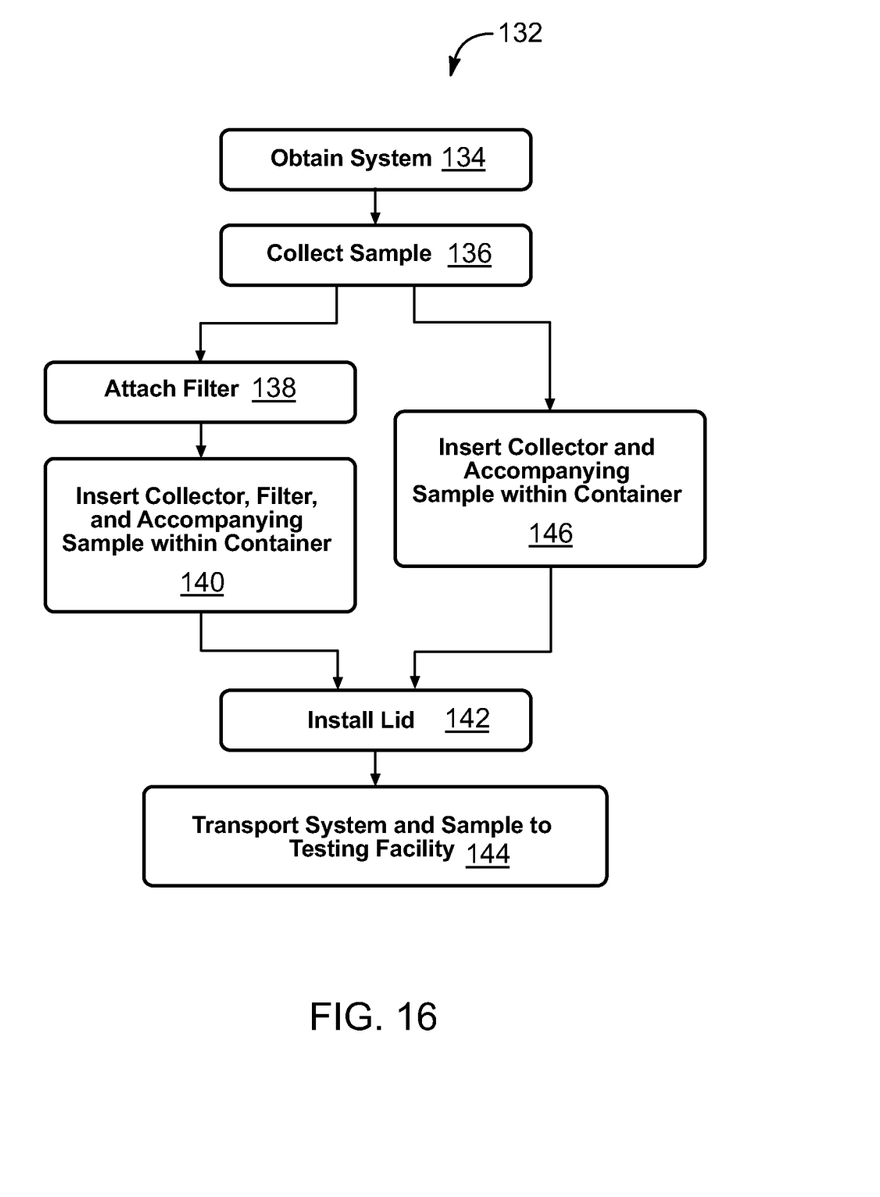
FIG. 16 is a schematic block diagram of one embodiment of a collection method in accordance with the present invention.

Referring to FIG. 16, in selected embodiments, the present invention may include a collection method 132. In one embodiment of a collection method 132, once a system 10 in accordance with the present invention has been obtained 134, a user may: (1) use a collector 30 to collect 136 a sample; (2) attach 138 a filter 50 to a distal end 44 of the collector 30; (3) insert 140 the collector 30, filter 50, and accompanying sample within a corresponding container 12; (4) install 142 a corresponding lid 90; and (5) transport 144 (e.g., ship) the system 10 and contained sample to a testing facility. Alternatively, a user may: (1) use a collector 30 to collect 136 a sample; (2) insert 146 the collector 30 and accompanying sample within a corresponding container 12; (3) install 142 a corresponding lid 90; and (4) transport 144 (e.g., ship) the system 10 and contained sample to a testing facility.

Figure 17:
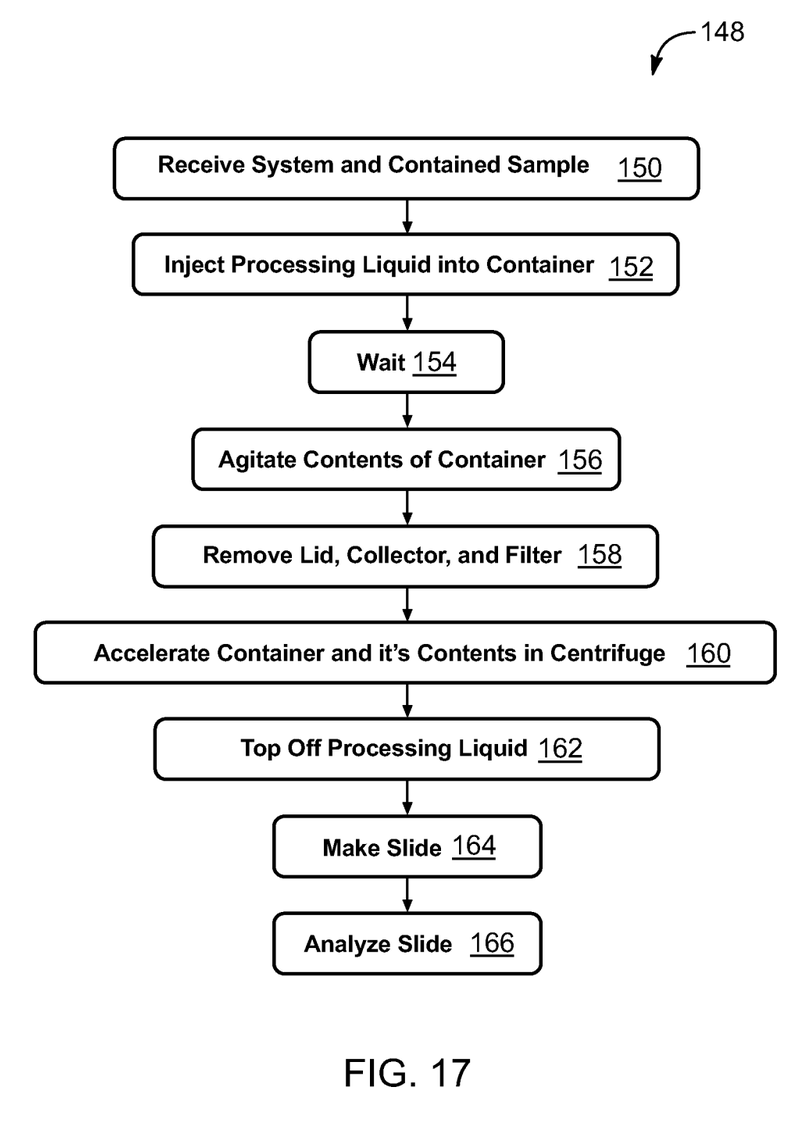
FIG. 17 is a schematic block diagram of one embodiment of an individual processing method in accordance with the present invention.

Referring to FIG. 17, the present invention may include an individualized processing method 148. In selected embodiments, an individualized processing method 148 may begin when a testing facility (e.g., laboratory) receives 150 a system 10 and contained sample for processing and testing. At the testing facility, a user (e.g., laboratory technician) may individually process a sample. This may include: (1) injecting 152 a processing liquid (e.g., a zinc sulfate solution) through a lid 90 and into a container 12; (2) waiting 154 a period of time for the processing liquid to dissolve, saturate, or break down the sample; (3) agitating 156 (e.g., moving the lid 90 up and down to move the collector 30 up and down with respect to the container 12) the contents of the container 12; (4) removing 158 the lid 90, collector 30, and (if included) the filter 50; (5) accelerating 160 the container and its contents within a centrifuge; (6) topping 162 off the container 12 with the processing liquid; (7) making 164 a slide; (8) analyzing 166 the slide under a microscope; and the like or combinations or sub-combinations thereof.

Figure 18:
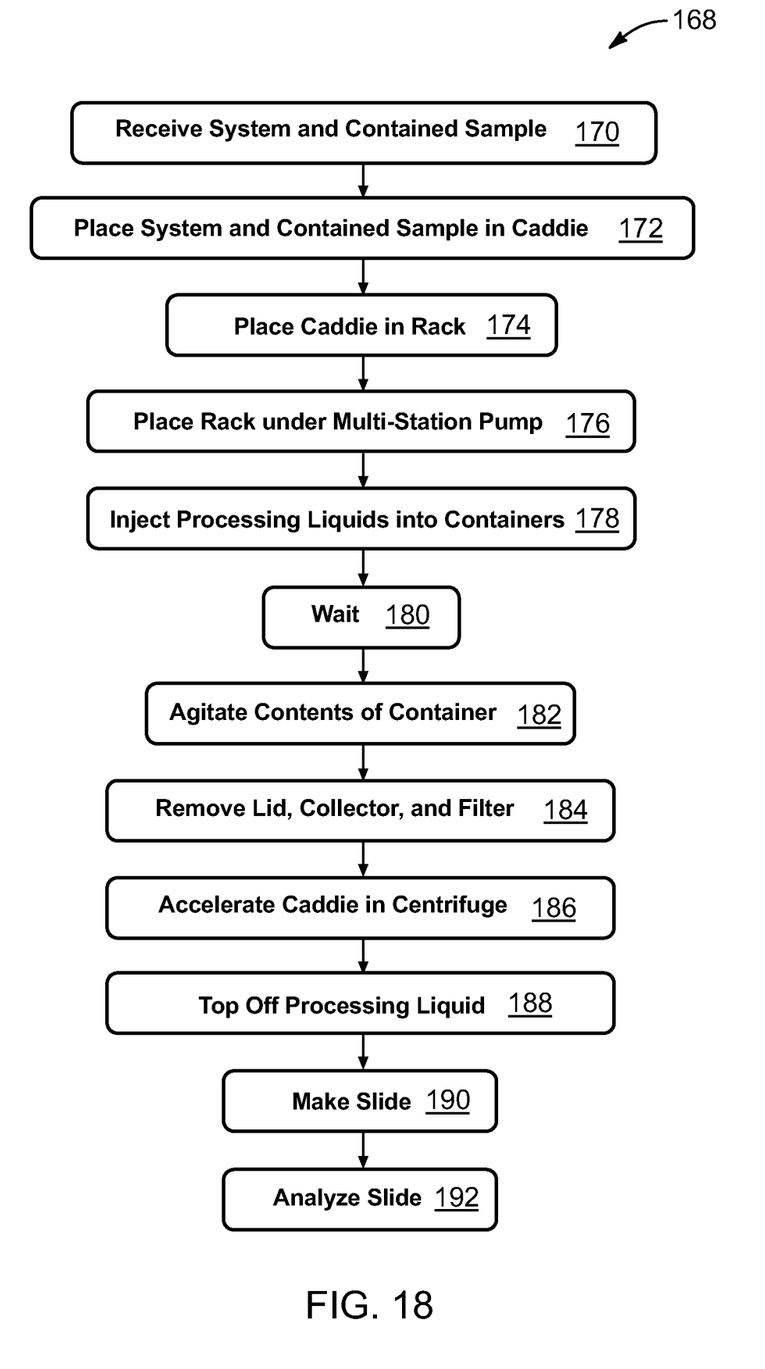
FIG. 18 is a schematic block diagram of one embodiment of a batch processing method in accordance with the present invention.

Referring to FIG. 18, the present invention may also include a batch processing method 168. In selected embodiments, a batch processing method 168 may begin when a testing facility receives 170 a plurality of systems 10 and contained samples for processing and testing. At the testing facility, one or more users may process the samples as a batch. This may include: (1) placing 172 each system 10 in a caddie or centrifuge adapter; (2) placing 174 each caddie in a rack; (3) placing 176 the rack under a multi-station pump; (4) injecting 176 (e.g., simultaneously) a processing liquid (e.g.,) through a lid 90 and into each container 12; (5) waiting 180 a period of time for the processing liquid to dissolve, saturate, or break down the samples; (6) agitating 182 (e.g., moving each lid 90 up and down to move a corresponding collector 30 up and down with respect to a corresponding container 12) the contents of the containers 12; (7) removing 184 each lid 90, collector 30, and (if included) filter 50; (8) accelerating 186 each caddie (and corresponding containers 12 and contents) within a centrifuge; (9) topping 188 off the containers 12 with the processing liquid; (10) making 190 slides; (11) analyzing 192 the slides under a microscope; and the like or combinations or sub-combinations thereof.

A caddie or centrifuge adapter in accordance with the present invention may be a structure configured to support a plurality of containers 12 (e.g., four to eight containers 12) in an upright orientation. A caddie may have a shape and size corresponding to a cavity within a centrifuge. Accordingly, rather than individually loading containers 12 into a centrifuge, a user may load a caddie (and all its contents) directly into a centrifuge in a single operation.

A rack in accordance with the present invention may be a structure configured to support one or more caddies (e.g., two to six caddies) in an upright orientation. In selected embodiments, a rack may index the caddies supported thereby. Accordingly, a rack may insure that containers 12 are consistently located in known locations with respect to the rack. Thus, by registering a rack with respect to a multi-station pump, each station may be positioned directly above the container 12 to which it will add processing liquid.

In selected embodiments, topping 162, 188 off a container 12 may include adding liquid to the container 12 until it is full (e.g., until a convex meniscus forms on the top of the container 12). Making 164, 190 a slide may include applying a cover slip to the top of a full container 12. The cover slip may contact the liquid within the container 12. Accordingly, material within the liquid (e.g., floating material) may collect on the cover slip. The cover slip may then be removed from the container 12 and placed on a microscope slide. Under a microscope, a user may analyze 166, 192 the material collected on the cover slip.

In selected embodiments, this material may include parasite identifiers from the corresponding fecal sample. Parasite identifiers may be any material evidencing the presence, type, and quantity of parasites afflicting the source of the sample. Parasite identifiers may include parasitic organisms, eggs or oocytes of parasitic organisms, remains of parasitic organisms or eggs, or the like or combinations or sub-combinations thereof.

A system 10 of the present invention may provide a method 148, 168 by which a single container 12 may be used at collection of a sample, during transport of the sample, and during processing of the sample at a testing facility. This may limit the risk of contaminating the sample and obtaining compromised or inaccurate test results. That is, a system 10 in accordance with the present invention may substantially reduce the risk of cross-contaminating or compromising a sample to be tested by limiting the need to transfer the sample from one container to another in the field and while processing of the sample within a testing facility. Additionally, such a system 10 may better protect users from undesirable exposure to samples, lower the time involved in processing samples, and the like.

In selected embodiments, methods in accordance with the present invention may enable expert analysis of a sample without requiring the sample to be shipped to an expert. For example, in certain embodiments, a sample may be collected 136 and a slide generated 164,190 using one or more of the steps described above. However, rather than analyzing 166, 192 a slide directly, an image of the slide may be generated. For example, a digital camera may capture through a microscope a digital copy (e.g., a still image, collection of still images, video clip, or the like) of the slide. This copy may then be transported (e.g., over a computer network) to an expert for analysis (e.g., for expert identification and counting of parasite identifiers).

In certain embodiments, methods in accordance with the present invention may avoid all shipping of a sample. For example, one or more steps of the collection 132 and processing 148, 168 methods may be performed at a single facility (e.g., a single veterinary laboratory). One or more slides generated 164, 190 in such methods 148, 168 may also be analyzed 166, 192 at the facility. However, if the expertise or personnel for performing such analysis is not present at the facility, an image of one or more slides may be generated and communicated in the manner described above to one or more qualified persons for analysis 166, 192. Accordingly, the sample itself may never leave the single facility.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A method comprising:
   obtaining a system comprising
      a container comprising a tube having an open end and a closed end opposite the open end,
      a collector comprising a shaft and a collection portion extending from an end of the shaft, and
      a lid comprising a cap portion, an elongated handle portion, and an aperture extending axially through the cap portion and the elongated handle portion;
   collecting, using the collector, a fecal sample;
   inserting, after the collecting, the fecal sample within the container;
   securing, after the inserting, the lid to the container such that the cap portion engages the open end of the tube, the elongated handle portion extends outside and away from the container, and the shaft of the collector extends through the cap portion and into the elongated handle portion by extending into the aperture;
   transporting, after the securing, the container with the fecal sample contained therewithin to a testing facility; and
   processing, at the testing facility, the fecal sample, the processing comprising introducing a liquid through the aperture and into the container while the lid remains secured to the container and accelerating the container in a centrifuge.

2. The method of claim 1, wherein the processing further comprises agitating the fecal sample within the liquid.

3. The method of claim 2, wherein the inserting further comprises inserting the collector within the container.

4. The method of claim 3, wherein the agitating comprises moving the collector with respect to the container.

5. The method of claim 3, wherein the processing further comprises removing the lid and collector from the container.

6. The method of claim 5, wherein the introducing, agitating, and removing occur prior to the accelerating.

7. The method of claim 6, wherein the system further comprises a filter.

8. The method of claim 7, further comprising attaching, after the collecting and before the inserting, the filter to a distal end of the collector.

9. The method of claim 8, wherein the inserting further comprises inserting the collector, fecal sample, and filter into the container with the filter located distal to the fecal sample.

10. The method of claim 9, wherein the removing further comprises:
   removing the lid, collector, and filter from the container; and
   removing, by the filter, one or more solids contained within the fecal sample from the container.

11. The method of claim 1, wherein the processing further comprises agitating the fecal sample within the liquid.

12. The method of claim 1, wherein the processing further comprises agitating the fecal sample within the liquid by moving the collector with respect to the container.

13. The method of claim 1, wherein the inserting further comprises inserting the collector within the container.

14. The method of claim 1, wherein the system further comprises a filter.

15. The method of claim 14, further comprising attaching, after the collecting and before the inserting, the filter to a distal end of the collector.

16. The method of claim 15, wherein the inserting further comprises inserting the collector, fecal sample, and filter into the container with the filter located distal to the fecal sample.

17. A method comprising:
   obtaining a system comprising
      a container comprising a tube having an open end and a closed end opposite the open end, a collector comprising a shaft and a collection portion extending from an end of the shaft, and a lid comprising a cap portion, an elongated handle portion, and an aperture extending axially through the cap portion and the elongated handle portion;

collecting, using the collector, a fecal sample;

inserting, after the collecting, the fecal sample within the container;

securing, after the inserting, the lid to the container such that the cap portion engages the open end of the tube, the elongated handle portion extends outside and away from the container, and the shaft of the collector extends through the cap portion and into the elongated handle portion by extending into the aperture;

transporting, after the securing, the container with the fecal sample contained therewithin to a testing facility; and processing, at the testing facility, the fecal sample, the processing comprising introducing a liquid through the aperture and into the container while the lid remains secured to the container and using a cover slip to collect, directly from the container, one or more parasite identifiers.

18. A method comprising:

obtaining a system comprising a container comprising a tube having an open end and a closed end opposite the open end, a collector comprising a shaft and a collection portion extending from an end of the shaft, and a lid comprising a cap portion, an elongated handle portion, a first aperture extending axially through the cap portion and the elongated handle portion, and a second aperture, independent of the first aperture, extending through the cap portion and the elongated handle portion;

collecting, using the collector, a fecal sample;

inserting, after the collecting, the fecal sample within the container;

securing, after the inserting, the lid to the container such that the cap portion engages the open end of the tube, the elongated handle portion extends outside and away from the container, and the shaft of the collector extends into the first aperture;

transporting, after the securing, the container with the fecal sample contained therewithin to a testing facility;

introducing, at the testing facility, a liquid through the first aperture and into the container while the lid remains secured to the container; and venting, during the introducing, gas contained within the container through the second aperture.

19. The method of claim 18, further comprising processing, at the testing facility, the fecal sample, the processing comprising accelerating the container in a centrifuge.

* * * * *